United States Patent [19]

Ozaki

[11] Patent Number: 5,034,969
[45] Date of Patent: Jul. 23, 1991

[54] TOMOGRAPHIC IMAGE DIAGNOSTIC METHOD AND APPARATUS INCLUDING AUTOMATIC ROI SETTING MEANS

[75] Inventor: Masahiro Ozaki, Ootawara, Japan

[73] Assignee: Kabushiki Kaisha Toshiba, Kanagawa, Japan

[21] Appl. No.: 437,014

[22] Filed: Nov. 15, 1989

[30] Foreign Application Priority Data

Nov. 16, 1988 [JP] Japan .................................. 63-287521

[51] Int. Cl.⁵ ........................... A61B 6/02; H05G 1/28
[52] U.S. Cl. ......................................... 378/18; 378/21; 378/4; 378/62; 378/163; 378/99; 378/162; 358/111
[58] Field of Search ................. 378/18, 21, 4, 64, 162, 378/62, 163, 99, 165, 207, 205; 382/6, 19, 41, 48; 358/111; 250/252.1 R

[56] References Cited

U.S. PATENT DOCUMENTS 4,233,507 11/1980 Volz ..................................... 378/207
4,782,502 11/1988 Schulz ..................................... 378/18

Primary Examiner—Constantine Hannaher
Assistant Examiner—Don Wong
Attorney, Agent, or Firm—Finnegan, Henderson, Farabow, Garrett and Dunner

[57] ABSTRACT

In a tomographic image diagnostic apparatus, a region of interest is automatically set on a tomographic image by recognizing actual positions of a phantom based upon CT (computerized tomographic) values of the phantom. The phantom is made of a base portion having a first reference CT value and a plurality of rods each having a second reference CT value. The region of interest is defined by recognizing the gravity centers of these rods. Said apparatus comprises: image memory for storing image data of an object and a phantom made of a plurality of reference substances and a base portion; a storage for previously storing a first reference CT value used for the base portion of the phantom, and also a second reference CT value used for each of the reference substances; a first detector for detecting a position of the phantom by comparing an actually measured first CT value of the base portion with the first reference CT value previously stored in the storage; a processor for performing both profile and filtering processes on the detected position of the phantom so as to obtain processed positional data of the phantom; a second detector for detecting positions of the reference substances contained in phantom by comparing an actually measured second CT value of each of the reference substances with the second reference CT value previously stored in the storage; and, a defining units for automatically defining a position of a region of interest with respect to the tomographic image data based upon the detected positions of the reference substances.

15 Claims, 19 Drawing Sheets

TOMOGRAPHIC IMAGE DIAGNOSTIC METHOD AND APPARATUS INCLUDING AUTOMATIC ROI SETTING MEANS

BACKGROUND OF THE INVENTION

1. Field of the Invention

The present invention generally relates to a method and apparatus for diagnosing tomographic images acquired by an X-ray CT (computerized tomography) apparatus, or an MRI (magnetic resonance imaging) apparatus. More specifically, the present invention is directed to a tomographic image diagnosing method and an apparatus capable of setting a region of interest on the tomographic image with the recognition on positions of reference substances imaged in the tomographic image.

2. Description of the Related Art

As a conventional method for measuring an amount of bone mineral contained in an object under medical examination, e.g., a patient by way of an X-ray CT apparatus, the following comparison method has been known in the art. That is, both the object under medical examination and a so-called "phantom", i.e., an article having a plurality of reference substances therein are simultaneously imaged, and thereafter a comparison is made between an averaged CT value of the bone of the patient and a CT value (i.e., an X-ray absorption value) of each of the reference substance. In FIG. 1, there is an example for utilizing such a phantom in conjunction with the X-ray CT apparatus. In this figure, an object 2 under examination is mounted on a couch plate 12 above a couch 30 of the X-ray CT apparatus 1. A plate-like curved phantom 3 is interposed between this object 2 and the couch plate 12.

FIG. 2 illustrates a shape of this phantom 3. FIG. 2A is a plan view of the phantom 3, and FIG. 2B is a cross-sectional view, taken along the line I—I' and viewed along an arrow direction. As apparent from FIG. 2B, a width "H" of the phantom 3 is substantially equal to another width "H" (see FIG. 1) of the couch plate 12. One major surface "M" of the phantom 3 is placed on the couch plate 12, whereas the other major surface "N" thereof receives the object 2 under examination thereon. A plurality of reference substances "13a" to "13e", so-called "rods", are provided within the phantom 3. These reference substances "13a" to "13e" contain different amounts of a known, constant substance (for example, $CaCO_3$) similar to the bone mineral. A base portion 15 in which no rod 13 is present is made of an urethane resin. Both the diameters of the respective rods and positions thereof are previously known. Both such a phantom 3 and the object 2 under medical examination are imaged by the X-ray CT apparatus 1 so as to obtain a CT (computerized tomographic) image as shown in FIG. 3. As previously explained, the plural rods 13a to 13e have been embedded within the phantom 3 on the couch plate 12, and the object 2 under examination is being positioned on the phantom 3. As shown in FIG. 3, regions of interest (referred to as "ROIs") "Ra" to "Rf" are successively set on the CT image by the manual operation of the operator with respect to the positions of the rods "13a" to "13e" and the bone 31 of the object 2 under medical examination. Since the respective pixels in the resultant image obtained by the X-ray CT apparatus 1 have the CT values inherently corresponding thereto, the amount of the bone mineral of the object 2 under examination can be predicted by comparing these CT values with the averaged CT values of the pixels of the respective ROIs "Ra" to "Rf". However, according to the above-described conventional ROI setting method, since ROIs "Ra" to "Rf" must be manually set by the operator while observing the CT image, the very cumbersome operation is necessarily unavoidable.

As another conventional ROI setting method with utilizing the positions of the rods contained in the phantom, another phantom 3' with a marker is employed as represented in FIG. 4. This phantom 3' contains a plurality of rods 13a' to 13e' similar to those of FIG. 2, and also two markers 32 and 33. These markers 32 and 33 have known very higher (or lower) CT values than the CT values of the organs inside the object 2 under examinations. FIG. 4A is a plan view of the phantom 3' and FIG. 4B is a cross-sectional view thereof, taken along a line J—J' and viewed along another arrow direction. It should be noted that the mutual positional relationships between the markers 32, 33 and rods 13a' to 13c' are previously known. In this conventional method, both the object 2 under examination and the phantom 3' with the markers 32 and 33 are simultaneously imaged by the X-ray CT apparatus 1, whereby a CT image as shown in FIG. 5 is acquired. Then, as the CT values of these markers 32 and 33 are already known, and there is no pixel having the CT value similar to those of the markers 32, 33, a measurement is carried out for the CT values of the respective pixels within the CT image, whereby the positions of these markers 32 and 33 of the phantom 3 can be readily recognized. Thus, as previously described, since the mutual positional relationships between the markers 32, 33 and the rods 13a' to 13e' are previously known, the positions of the respective rods 13a' to 13e' can be readily recognized. As a result, regions of interest (ROIs) can be set for the positions of the respective rods. However, according to the second conventional method, it is not possible to use a normal phantom, i.e., a phantom having no marker. The manufacture cost of such a specific phantom having markers becomes extremely high, as compared with the normal phantom without any marker.

Moreover, the similar disadvantages to those of the above-described X-ray CT apparatus are caused in another phantom containing the rods which have different water contents when this phantom is imaged in an MRI apparatus.

As previously described, in the conventional method where the positions of the reference substances contained in the phantom are recognized so as to set the regions of interest, the positions of ROIs must be manually set by an operator in case of using the normal phantom without markers. Moreover, the specific phantom with markers is required so as to set ROIs. In particular, when employing such a specific phantom, there are great possibilities that an artifact may occur from the marker, which will give an adverse influence to the image information required for the diagnosis.

The present invention has been made in an attempt to solve the above-described problems of the conventional ROI setting methods, and therefore has an object to provide such a tomographic image diagnostic method and also a tomographic image diagnostic apparatus capable of automatically recognizing positions of reference substances and also automatically setting a region of interest by employing the normal phantom having no marker without any cumbersome operation by an operator.

SUMMARY OF THE INVENTION

To achieve the above-described objects and other features of the present invention, it is therefore provided a method for automatically setting a region of interest in a tomographic image, comprising the steps of:

imaging both an object (2) under medical examination and a phantom (3) made of a plurality of reference substances (13a; 13e) and a base portion (15) thereof so a to produce a tomographic image, said base portion (15) having a first known CT (computerized tomographic) value and said reference substances (13a: 13e) each having a second same known CT value different from said first CT value;

first reading the first known CT value corresponding to each pixel within an area designated in said base portion (15) so as to recognize a position of said base portion (15) with respect to the tomographic image;

first setting a pattern (16) having a predetermined shape to the tomographic image based upon the recognized position of the base portion (13);

second reading the second known CT value corresponding to each pixel located on the pattern (176) so as to recognize positions of the reference substances (13a:13e). and, second setting a region of interest (18a: 18e) to the tomographic image based upon the recognized positions of said reference substances (13a: 13e).

Furthermore, a tomographic image diagnostic apparatus according to the invention comprises:

means (1) for imaging both an object (2) under medical examination and a phantom (3) made of a plurality of reference substances (13a: 13e) and a base portion (15) so as to produce tomographic image data thereof, said base portion (15) has a first known CT (computerized tomographic) value and said reference substances (13a: 13e) each having a second same known CT value different from said first CT value:

memory means (4) for storing said tomographic image data with said first and second CT values;

first CT value designating means (7) for designating an area used to measure said first CT value and also for designating a first CT value range of said base portion (15) with respect to said tomographic image data stored in said memory means (4);

CT value measuring (8) for measuring said first CT value of each pixel within said designated area so as to extract a region having a predetermined CT value within said first CT value range of said base portion (15);

second CT value designating means (9) for designating a second CT value range of said reference substances (13a: 13e) based upon the extracted region, and also for setting a pattern (16) having a predetermined shape on said tomographic image data; and, means (10) for recognizing positions of said reference substances (13a; 13e) with respect to the tomographic image data based upon said second CT value range thereof so as to automatically set a region of interest to said tomographic image data.

BRIEF DESCRIPTION OF THE DRAWINGS

For a better understanding of the present invention, reference is made to the following descriptions in conjunction with the accompanying drawings; in which:

FIG. 12 schematically represents a functional diagram of the X-ray CT diagnostic apparatus 100 shown in FIG. 6;

DETAILED DESCRIPTION OF THE PREFERRED EMBODIMENTS

ARRANGEMENT OF X-RAY CT DIAGNOSTIC APPARATUS

Figure 6:
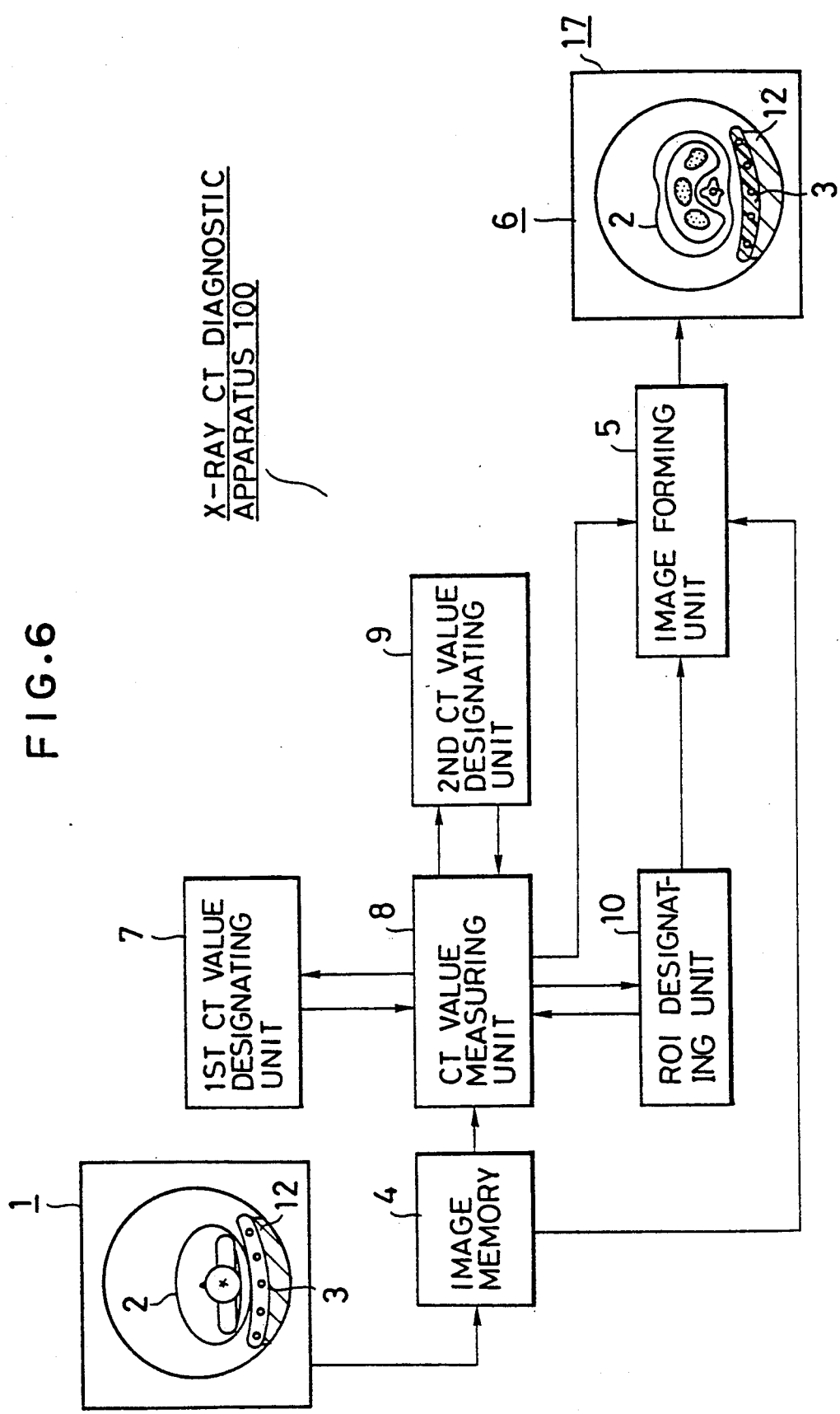
FIG. 6 is a schematic block diagram of an X-ray CT diagnostic apparatus 100 according to a first preferred embodiment of the invention.

Referring now to FIG. 6, an overall arrangement of an X-ray CT (computerized tomographic) diagnostic apparatus 100 according to a first preferred embodiment of the invention, in conjunction with the known X-ray CT apparatus 1.

The X-ray CT diagnostic apparatus 100 is so arranged as follows.

After both the object 2 under medical examination (i.e., a patient) and the normal phantom 3 without markers have been imaged by the X-ray CT (computerized tomography) apparatus 1 to obtain tomographic image data are stored in an image memory 4 as image data indicative of CT values (i.e., X-ray absorption values) with respect to the respective pixels. The entire image has been subdivided into a matrix form constructed of, for instance, 512×512 pixels. The CT value data thus stored in the image memory 4 are window-processed in an image forming unit 5 so as to form tomographic images. Then, the tomographic images are displayed on a display unit 6 such as a cathode-ray tube. A first CT value designating unit 7 is employed so as to designate a region where the CT values are measured, and a range of the CT values in order that the CT value of the base portion 15 of this phantom 3 is recognized by the CT value measuring unit 8. The CT value measuring unit 8 has a function to read out the CT value with respect to each of the pixels within a portion of the memory regions of the image memory 4, and to pick up the region having the CT value that is within the range of the CT value of base portion 15. Based upon the region extracted by this CT value measuring unit 8 as a reference value, another CT value range for the rod 13 of the phantom 3 is designated by a second CT value designating unit 9. In addition, a pattern or figure such as a circle is set on the image and thus the set pattern is displayed on the display unit 6. Subsequently, the CT values of the respective pixels along the outer circumference of the circle which has been set by the second CT value designating unit 9, are read out from the image memory 4 by the CT value measuring unit 8. Accordingly, the regions having the CT values corresponding to the CT value range of the rod 13 are extracted. With the above-described arrangements, the positions of the rods 13 embedded in the phantom 3 which are displayed in the tomographic image can be automatically recognized by the X-ray CT diagnostic apparatus 100. Furthermore, with respect to the extracted positions of the rods 13, a region of interest (referred to as a "ROI") having an appropriate shape such as a circle of a predetermined radius can be automatically set by a ROI designating unit 10, and also the CT values of the respective rods 13 within the phantom 3 can be automatically measured by reading the averaged CT value within ROI from the image memory 4, and by measuring those by the CT value measuring unit 8.

Overall Operation of First Automatic ROI Setting Operation

Figure 7:
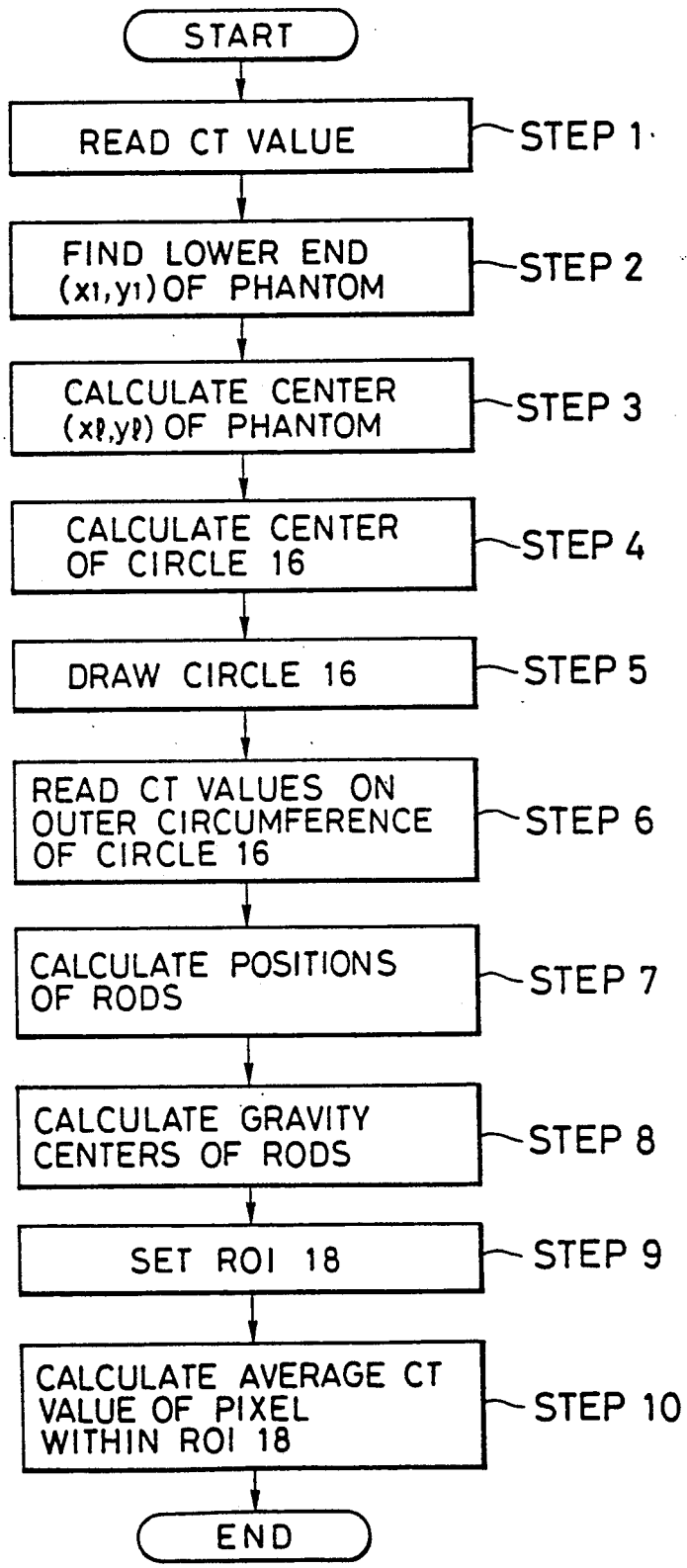
FIG. 7 is a flowchart for explaining an automatic ROI setting method employed in the X-ray CT diagnostic apparatus 100 shown in FIG. 6.

FIG. 7 is a flowchart for explaining an overall operation of an automatic ROI (region of interest) setting operation according to a first preferred embodiment of the invention.

Figure 8:
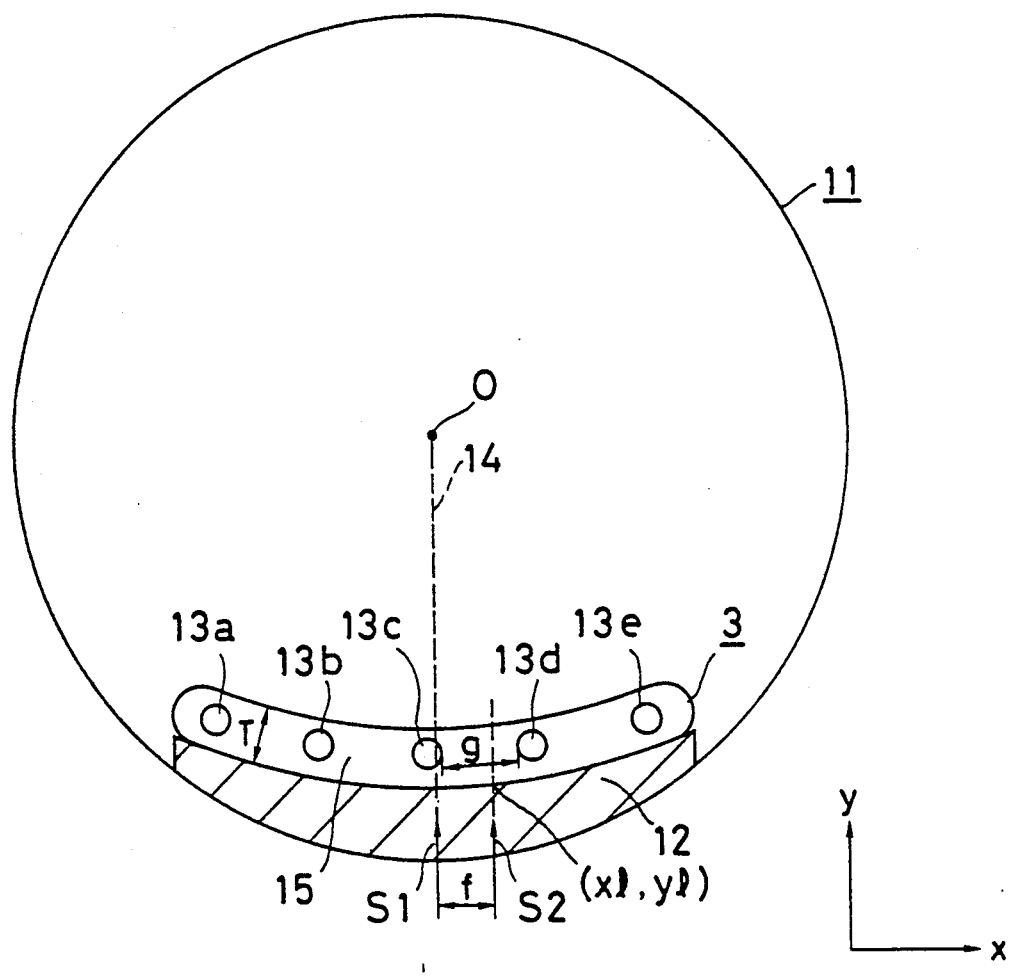
FIGS. 8, 9, 12 and 14 illustrate the first automatic ROI setting method of FIG. 7.

In a first step 1, CT (computerized tomographic) values of the respective pixels are read out from a predetermined position as a starting point within the CT image toward a predetermined therein. In FIG. 8, there is shown an illustration for explaining the readout method of the CT values defined at the step 1. In this drawing, the couch plate 12 of the X-ray CT apparatus 1 and the normal phantom 3 including the five rods "13a" to "13e" are imaged within the imaging area 11 representative of the region which has been imaged by the X-ray CT apparatus 1 and reconstructed thereby. It should be noted that the horizontal right-hand direction denotes "X" whereas the vertical direction indicates "y" as viewed in FIG. 8. In the first preferred embodiment, the CT values with respect to the respective pixels are read out along two paths toward the y-direction from two points S1 and S2. The first point S1 corresponds to a point at which a straight line 14 cross with the outer circumference of the imaging area 11. This straight line 14 is drawn from the center "O" of this imaging area 11 toward the y-direction. The second point S2 is remote from this straight line 14 by a distance "f" in the x-direction.

Assuming now that the read CT values are "Px" and the known CT value of the base 15 of the phantom 3 is "$P_o$", the read operation is continued until "n" pieces of the pixels capable of satisfying the following formula (1) are continued.

$$P_x - P_o F \text{ (allowable range)} \qquad (1)$$

It should be noted that the above-described "n" is a known value, and is smaller than the number of the pixels corresponding to the thickness "T" of the phantom "3" which is also known in the image, and the allowable range is also the known value. If there exists the rod 13 on the readout path when reading out the CT values, the above-described formula (1) is not satisfied. To avoid such a problem, the CT values are read with respect to two paths separated with each other by a distance "f" according to the preferred embodiment. This distance "f" between the adjacent rods, e.g., 13c and 13d (see FIG. 8). As a result, at least one path does not contain the rod 13. After the CT values have been read out as to the above-described two paths, the position of the first pixel which can satisfy the formula (1) is determined as the coordinate of the lower end of the phantom 3 ($x_p$, $y_p$) at a step 2. That is, the pixel coordinate position is defined as to one path for satisfying the formula (1), or either path in case that both paths can satisfy the formula (1), for instance, the path starting from a point "S2".

Figure 9:
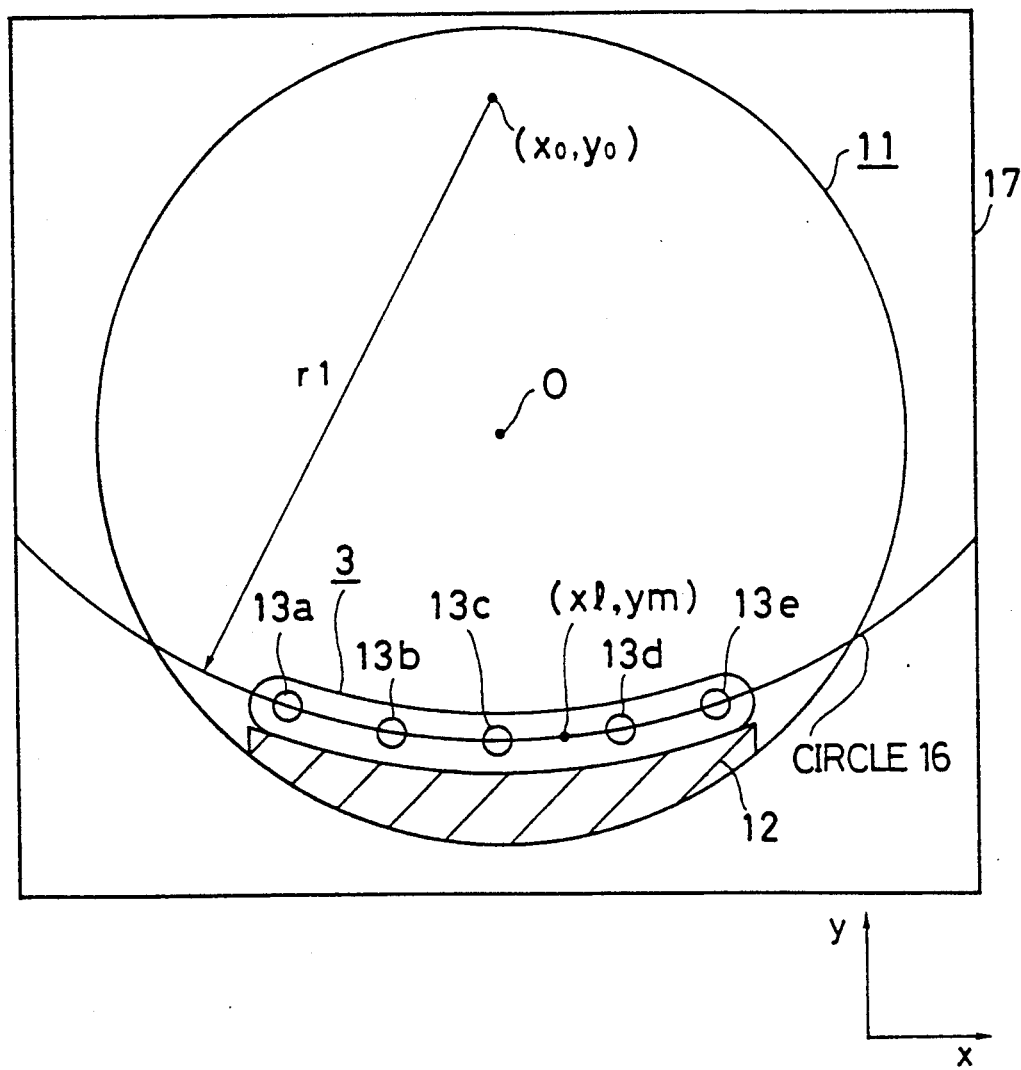

Subsequently, assuming that the thickness of the phantom 3 per se is "T", a y-coordinate value "$y_a$" of a center of the phantom 3 at a position "$x_p$" of the x-coordinate in the thickness direction will be calculated, as shown in FIG. 9., in accordance with the following equation (2) by employing the y-coordinate value "$y_m$" which has been calculated at the step 3.

$$y_m = y_p + T/2 \qquad (2)$$

In a step 4, a determination is made to a position of a pattern or figure set by the second CT value designating unit 9 represented in FIG. 6 based upon the y-coordinate value "$y_m$" of the center of the phantom 3 along the thickness "T" thereof calculated in the previous step 3. In the first preferred embodiment, this pattern corresponds to a circle 16 having a predetermined radius, as shown in FIG. 9, depending upon the shape of this phantom 3. This radius is necessarily determined by the shape of the phantom 3, i.e., a distance "rl" from the center of the curvature of the curved surface to a center point of the thickness "T" of the phantom 3. As illustrated in FIG. 9, there are some possibilities that the circle 16 is located outside the screen 17. It should be understood from the arrangement of the X-ray CT apparatus that the x-coordinate of the couch plate 12 does not change within the imaging area 11 at all, and the x-coordinate of the center "o" within the imaging area 11 is coincident with the x-coordinate of the center of the couch plate 12 along the width "T". As a result, assuming that the center position of the circle 16 is defined as ($x_o$, $y_o$); "$x_o$" is coincident with the x-coordinate of the center "o" of the imaging area 11. The center position of "$y_o$" will be calculated as follows.

$$y_o = y_m + \sqrt{(r_1^2 - (x_p - x_o)^2} \qquad (3)$$

In accordance with the position determined at the above step 4, the circle 16 is drawn on the display screen 17 at a step 5.

Figure 10A:
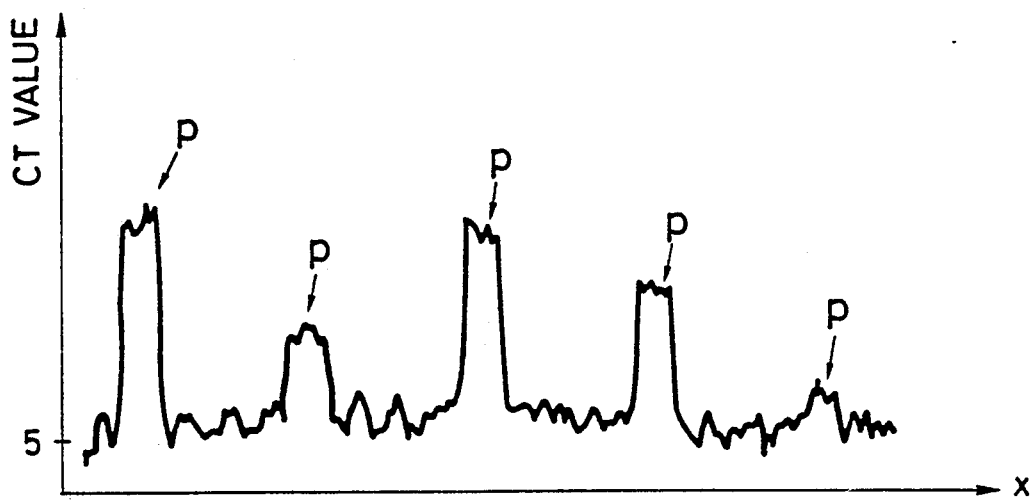
FIGS. 10A to 11B are graphic representations for showing CT values of the rods within the phantom 3 of FIG. 6.

Once the circle 16 is drawn on the display screen 17 at the step 5, the CT values as to the respective pixels on the outer circumference of the circle 16 are read out at a next step 6. This CT value reading operation is performed within either a range of a lower half portion of this circle 16, or another range imaged on the display screen 17. As a result of the CT value reading operation, data as represented in FIG. 10A are obtained. In the graphic representation shown in FIG. 10A, an abscissa indicates the x-coordinate on the outer circumference of the circle 16, whereas an ordinate indicates the CT value.

Figure 1:
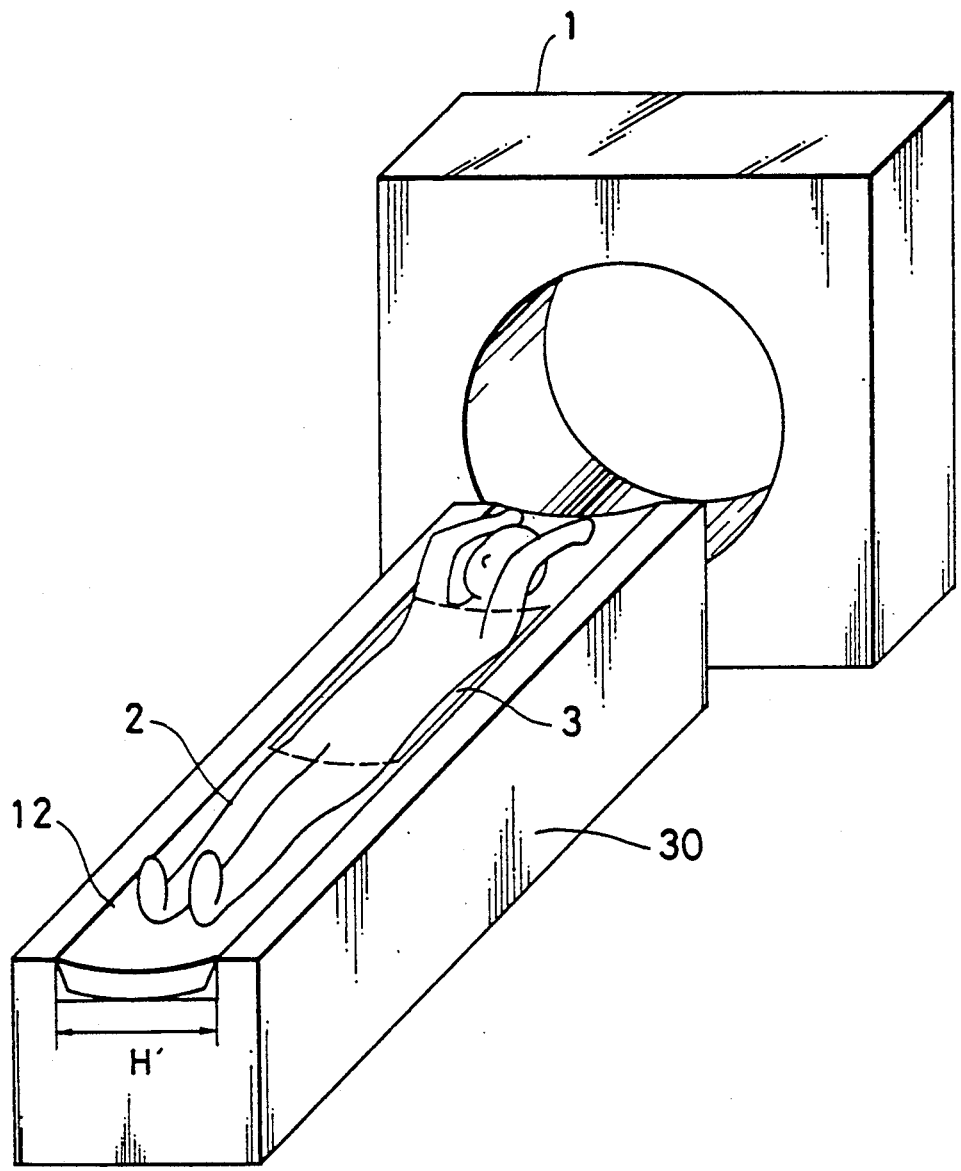
FIG. 1 schematically illustrates an X-ray CT apparatus with use of a normal phantom.
Figure 2A:
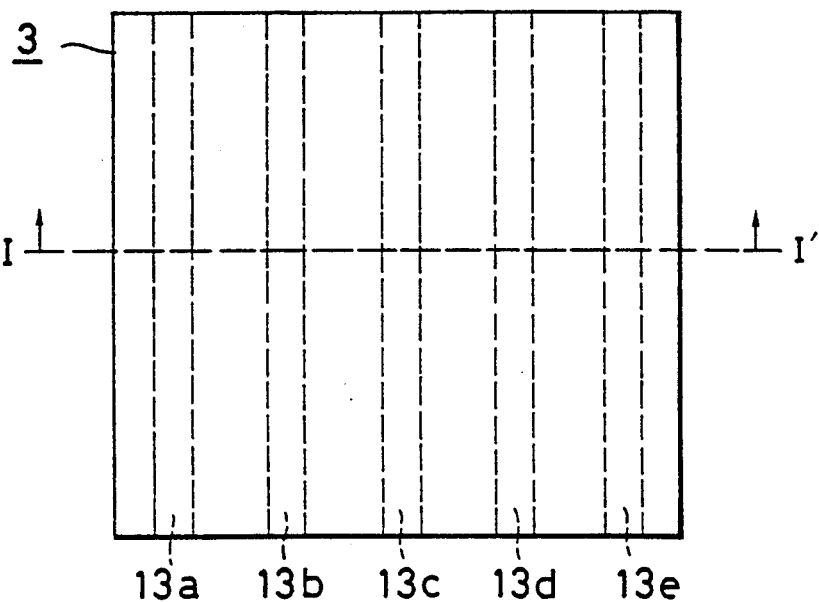
FIGS. 2 and 3 are one conventional phantom and a tomographic image thereof.
Figure 2B:
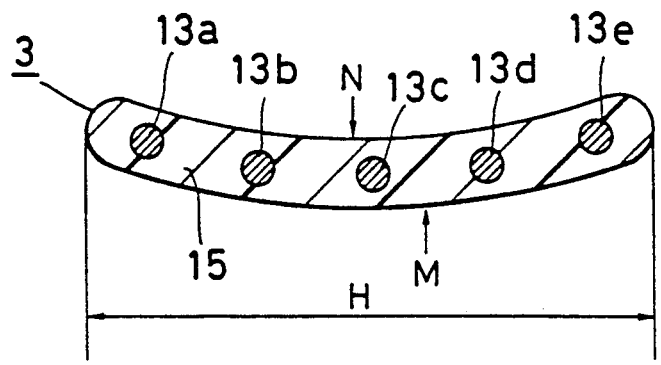
Figure 3:
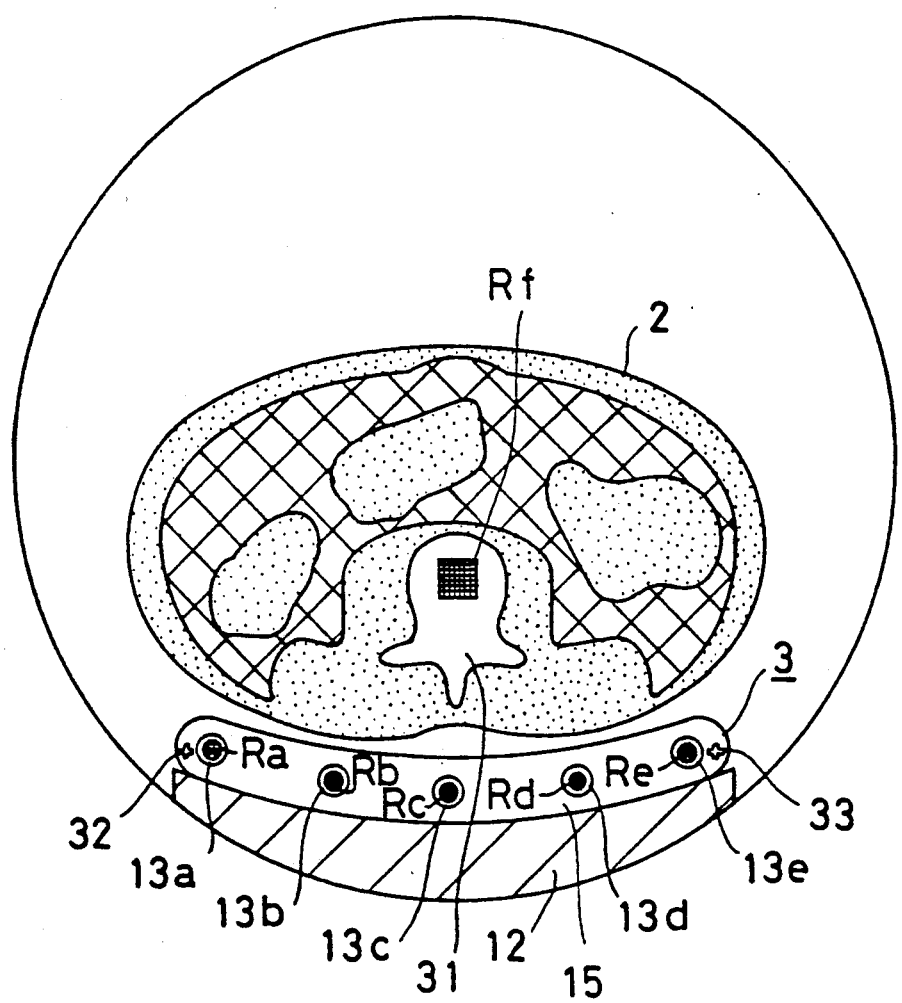
Figure 4A:
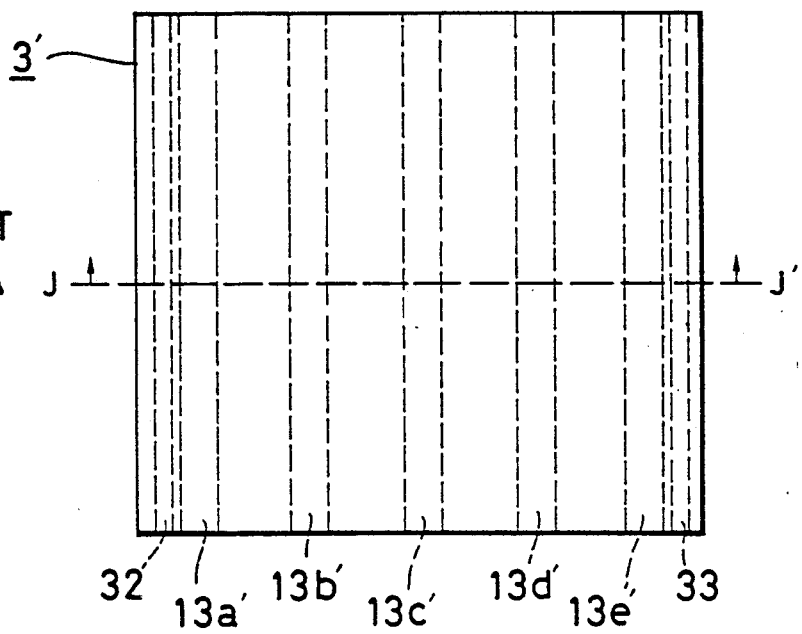
FIGS. 4 and 5 are another conventional phantom and a tomographic image thereof.
Figure 4B:
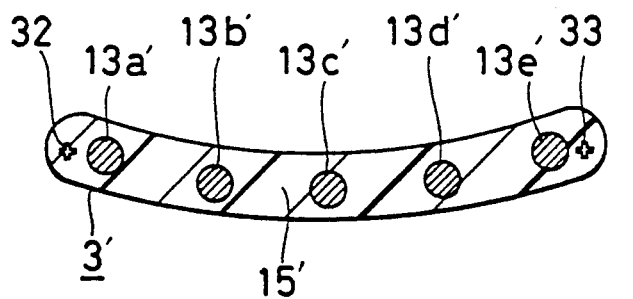
Figure 5:
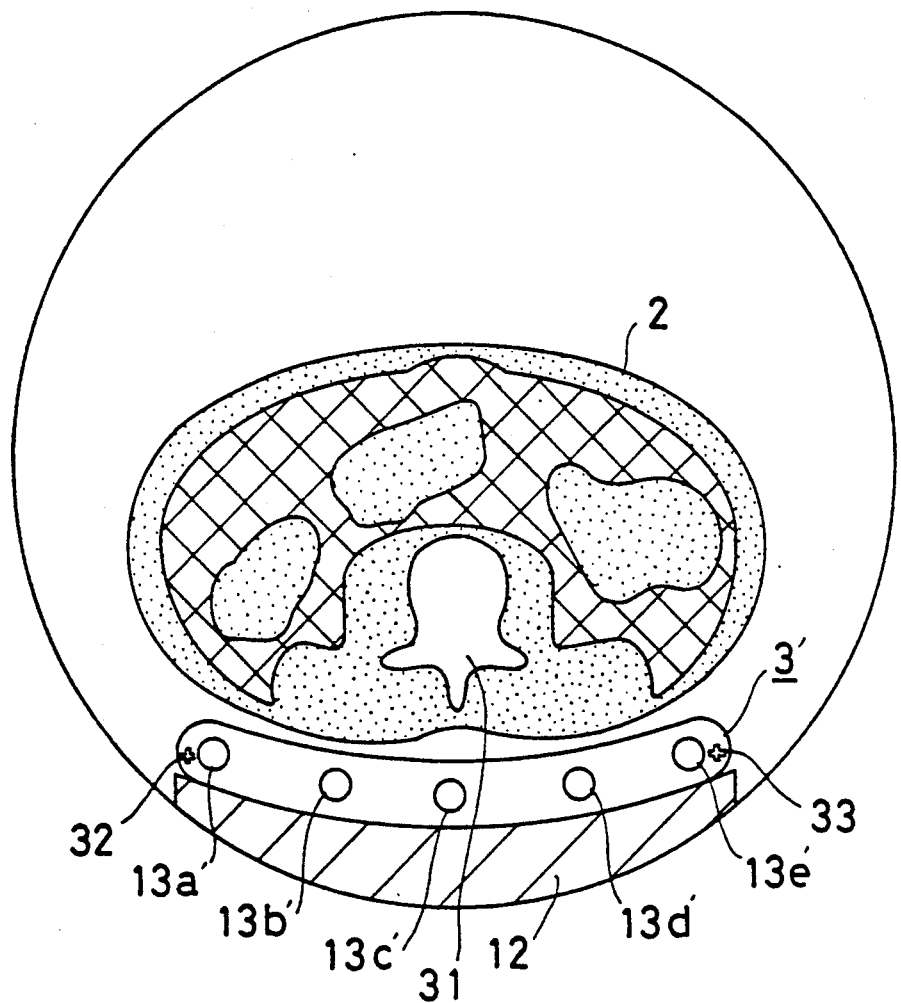
Figure 10B:
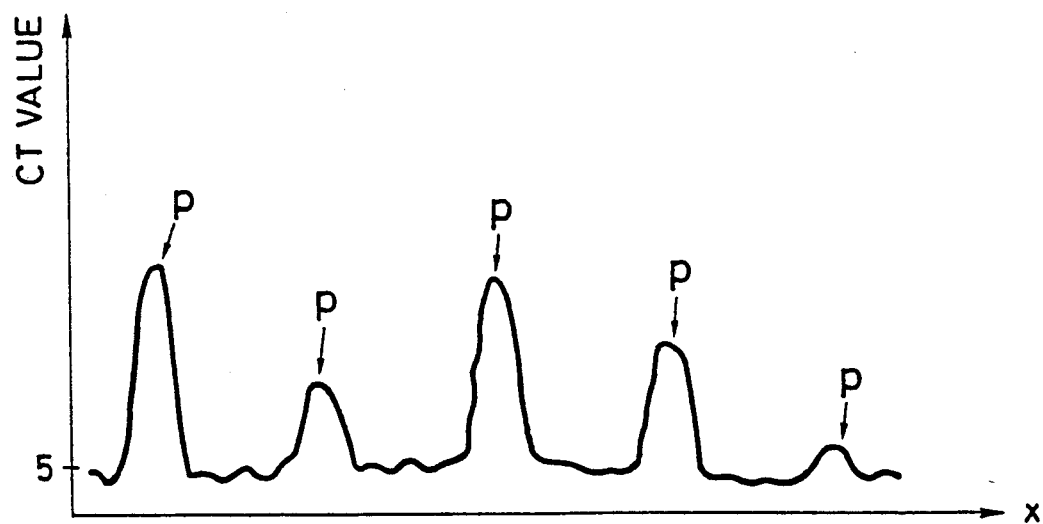

It should be noted that there are some level shifts as a whole between the actual CT values of the phantom 3 and the measured CT values. In FIG. 10A, for instance, since the portions having the lower CT values other than the peak portions "p" of the CT values represent the CT values of the portions other than the rods 13 contained in the phantom 3, i.e., an urethane resin, the CT values of the first-mentioned portions must be on the order of 5 (the CT value of water corresponds to "0"). However, most of these CT values are higher than 5. To correct such level shifts, the CT values of the regions in the phantom 3, which are not obviously equal to the rod 13, namely the base region 15 shown in FIG. 3 are subtracted from the CT values of the read overall pixels. It should be noted that as the CT value of the base portion 15, an average CT value over the entire pixels of the base portion is utilized, since the pixels having CT values within a predetermined CT value range are regarded as the above-described base portion 15. Furthermore, according to the first preferred embodiment, the above-described data are smoothing-processed in the CT value measuring unit 8 shown in FIG. 6 so as to diminish the adverse influence caused by the noise, whereby data represented in FIG. 10B are finally acquired. As compared with the data shown in FIG. 10A, the peak portions "p" are clearly distinguishable from other portions in the data shown in FIG. 10B. As apparent from FIG. 10B, the CT values of the portions other than the peak portions "p" are on the order of 5.

Figure 11A:
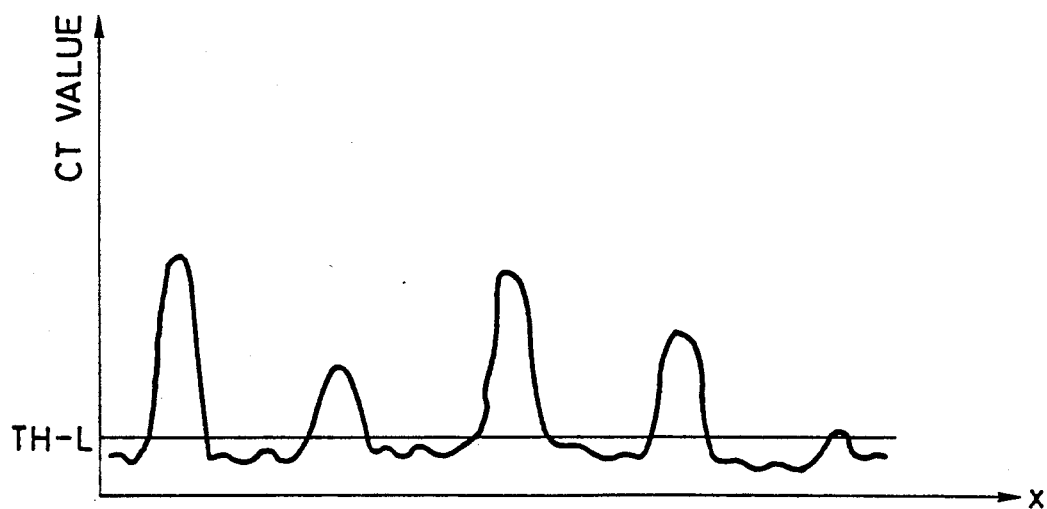
Figure 11B:
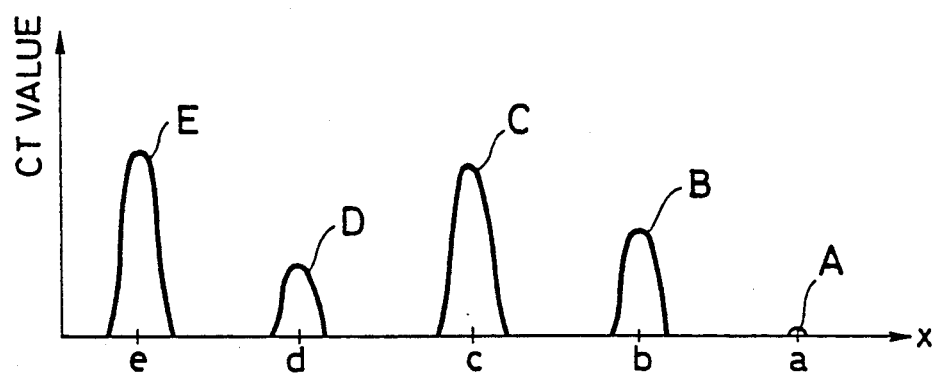

Thereafter, a threshold level "TH-L" representative of a certain CT value shown in FIG. 11A is preset for the data acquired in the step shown in FIG. 10B. When the pixels having the CT values higher than this threshold level "TH-L" are extracted, regions "A" to "E" corresponding to the perspective rods 13a to 13e shown in FIG. 11B are extracted. Thus, positions "a" to "e" which are obtained by dividing each width of the respective regions "A" to "E" into a half width thereof, are determined as approximate positions of these rods 13a to 13e (step 7). It should be noted that the coordinate of i-th rod calculated at the step 7 is $(x_i, y_i)$.

After the approximate coordinate $(x_i, y_i)$ of the rod has been determined, a coordinate of a gravity center of the rod is calculated based on this coordinate $(x_i, y_i)$ in a step 8. A detailed operation defined at the step 8 will now be described later.

Figure 12:
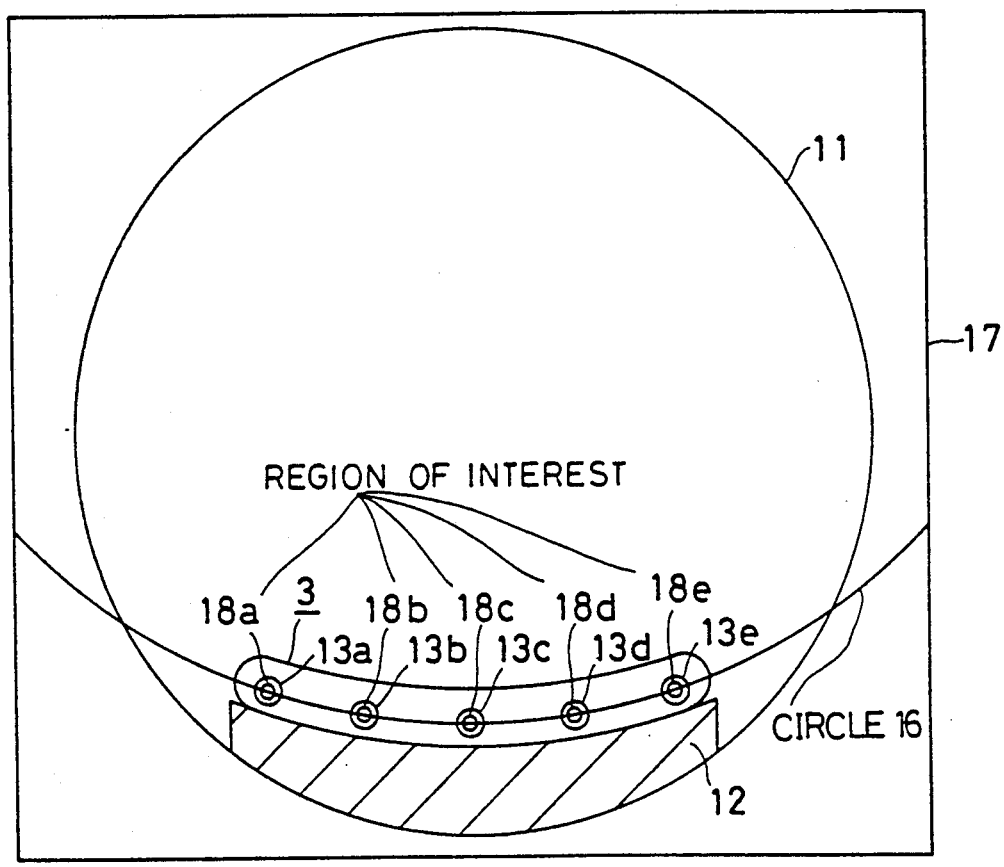

Once the gravity center of the rod 13 has been calculated, a circular ROI (region of interest) 18a having a radius smaller than the diameter of the known rod, for instance, "13a" is set as represented in FIG. 12 with respect to a center as the predetermined gravity center (step 9).

When this ROI 18a has been set, the CT values of the respective pixels within ROI 18a are measured and an averaged CT value of entire pixels is regarded as a CT value for the rod (step 10). The above-described operations defined by the steps 1 to 10 are carried out with respect to the remaining rods 13b to 13e in order to automatically recognize the positions in the image for the remaining rods 13b to 13e, and furthermore to automatically set ROIs 18a to 18e as illustrated in FIG. 12.

CALCULATION ON GRAVITY CENTER OF ROD

Figure 13:
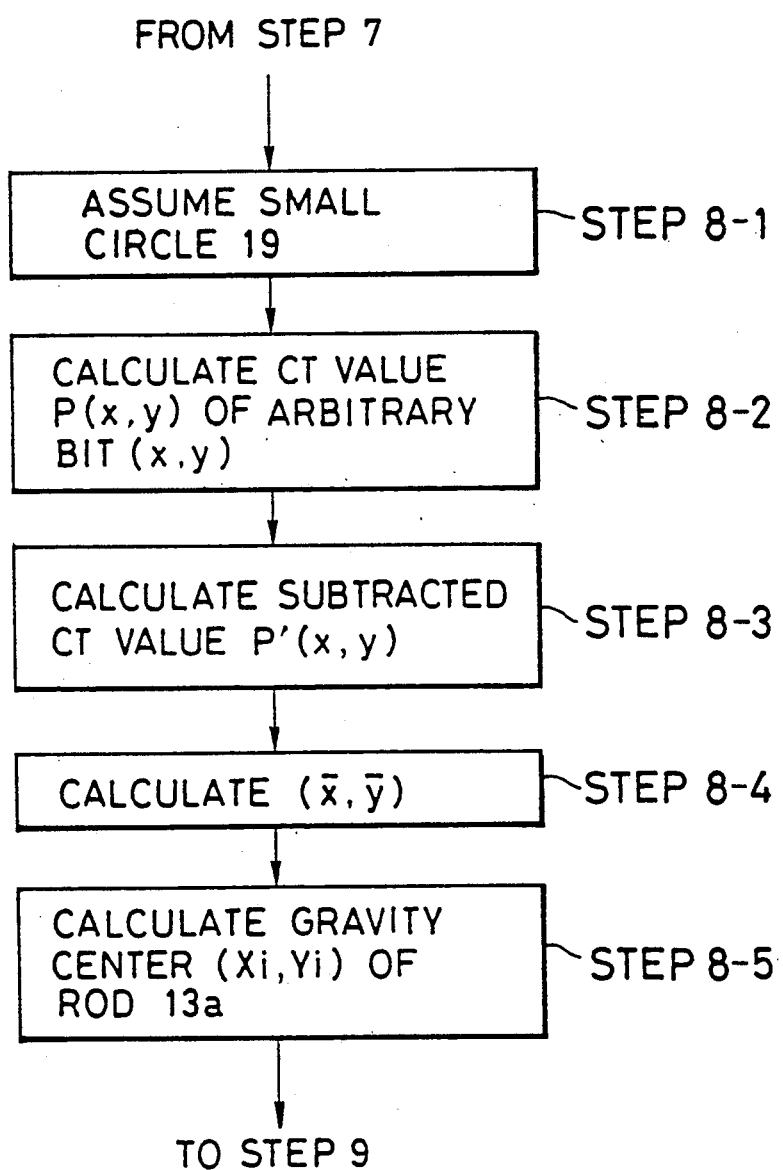
FIG. 13 is a flowchart for explaining a detailed operation of the gravity center calculation process defined at the step 8 shown in FIG. 7.
Figure 14:
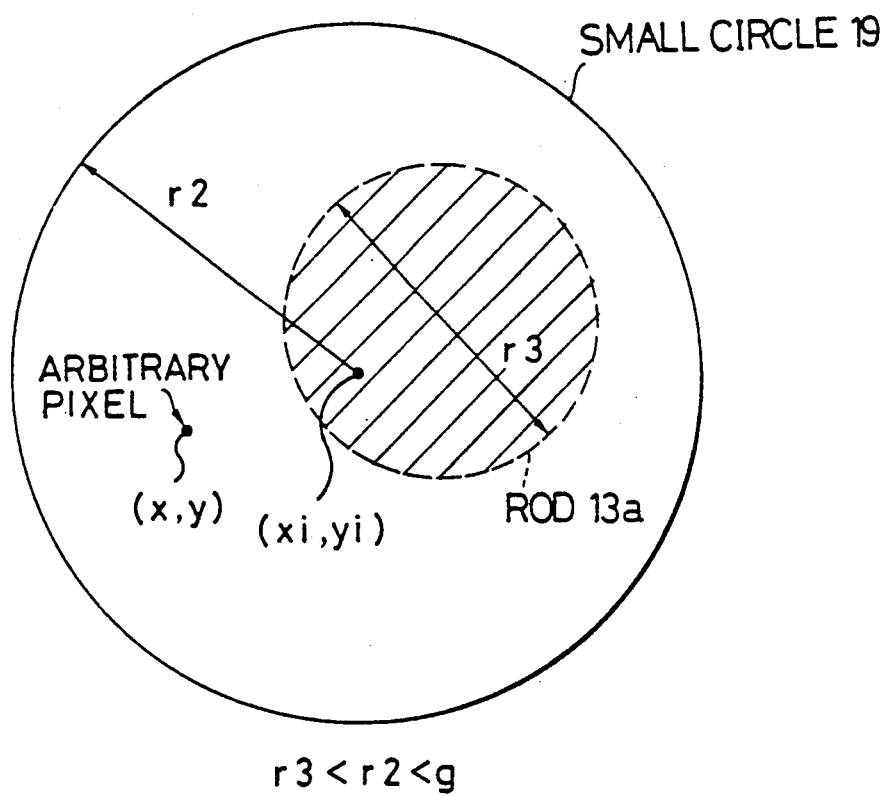

FIG. 13 is a flowchart for explaining a detailed operation of the above-described step 8, i.e., the calculation on the gravity center of the rod.

At first, as to a certain rod, e.g., 13a (see FIG. 8), a circle 19 having a radius "r2" is assumed with respect to a point $(x_i, y_i)$ as a center (step 8-1). This radius "r2" is greater than the diameter r3 of the rod 13a and shorter than the distance "g" between the successive rods 13 shown in FIG. 8. Then, in the subsequent step 8-2, assuming that the coordinate representative of the position of the arbitrary pixel within this circle 19 is (x, y), and the CT values corresponding to the respective pixels are p(x, y), the CT values p(x, y) with respect to the respective pixels within the circle 19 are calculated. Thereafter, to clearly discriminate the CT values of the rod portion 13a from that of the base portion 15, the CT value of the base portion 15 is equal to "0" as indicated in the following formula (4) and the other CT values of the rod portion 15 are obtained by subtracting the CT values of base portion 15 as represented in the following formula (5), i.e., P'(x, y) at a step 8-3.

If p'(x, y) F $p_o$+(allowable range), then $$p'(x, y) = 0 \quad (4).$$

If p(x, y) $p_o$+(allowable range), then $$p'(x, y) = p(x, y) - P_o \quad (5),$$

where "$P_o$" denotes the CT values of the base portion 15 of the phantom 3, and the allowable range is a known value.

Then, by employing the CT values p(x, y) calculated in the step 8-3, difference (x, y) between the point $(x_i, y_i)$ calculated at the previous step 7 and the x, y-coordinates of the gravity center $(X_i, Y_i)$ are calculated in accordance with the following formulae (6) and (7) as to all of the coordinates $\bar{x}, \bar{y}$ within the circle 19) step 8-4).

$$x = \frac{S(x - x_i) * p'(x,y)}{p'(x,y)} \quad (6)$$

$$y = \frac{S(y - y_i) * p'(x,y)}{p'(x,y)} \quad (7)$$

Based upon $(x_i, y_i)$ and (x, y) calculated at the previous steps 7 and 8, the gravity center $(X_i, Y_i)$ of the rod 13a is calculated from the following formula (8) at a step 8-5.

$$(X_i, Y_i) = (X_i + X, Y_i + Y) \quad (8)$$

After the above-described steps 8-1 to 8-5 have been accomplished, the process returns to the step 9 as represented in FIG. 7.

OVERALL FIRST ROI SETTING SYSTEM

Figure 15:
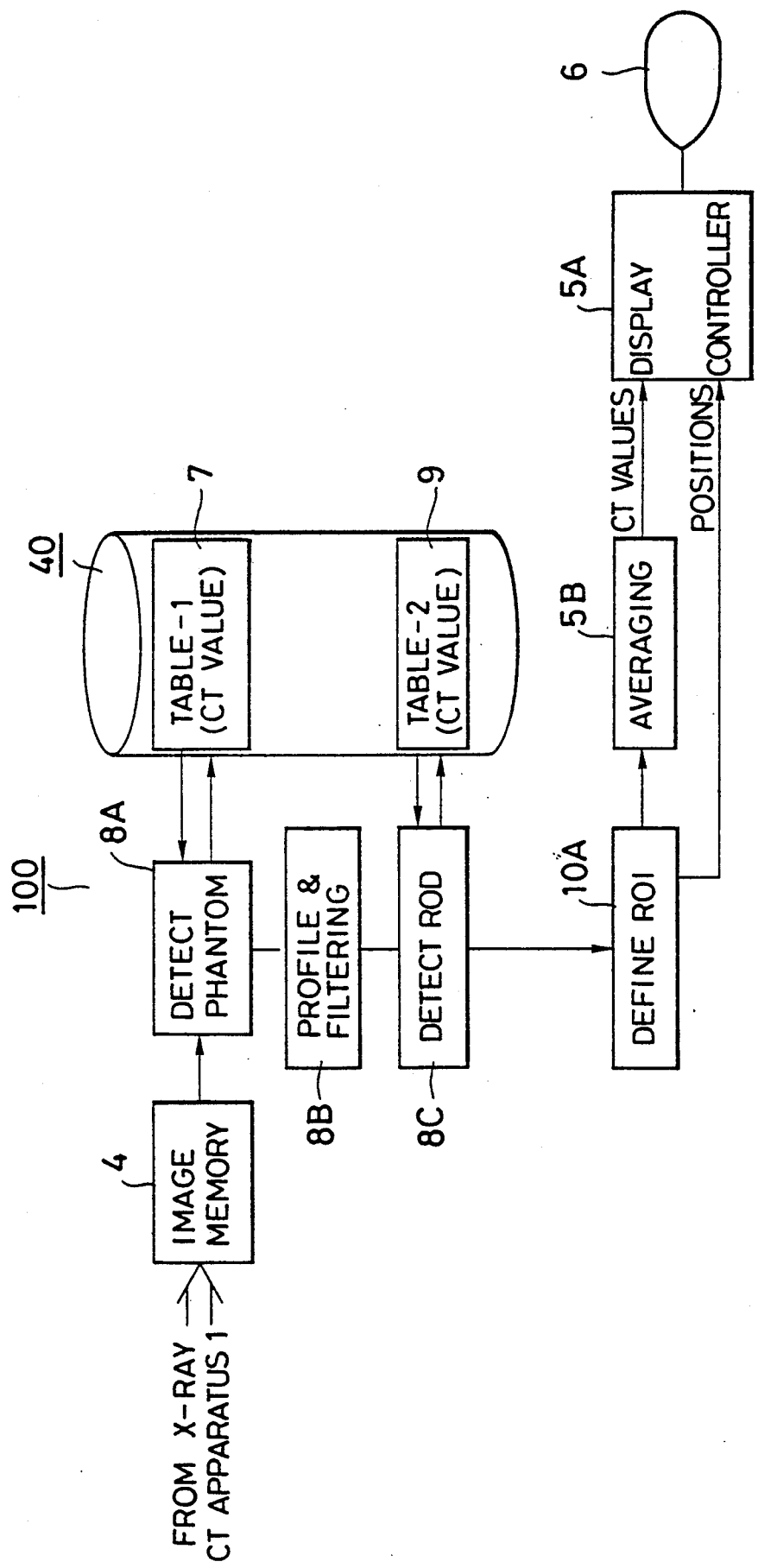

Referring now to a functional block diagram shown in FIG. 15, the automatic ROI setting system according to a first preferred embodiment will be summarized.

In the functional block diagram of FIG. 15, based upon the imaging data derived from the imaging memory 4, a detection is made on the phantom 3 in a first function block 8A. In this case, the first reference CT value for the base portion 15 has been stored in a table-1 of a magnetic drum 40, and the first reference CT value is fetched and compared with an actually measured first CT value so as to detect the phantom 3. Thereafter, in a second function block 8B, both profile and filtering processes are carried out. Furthermore, a detection is made to the position of the rod 13 in a third function block 8C, since the second reference CT values for the rod 13 have been stored in a table-2 of the magnetic drum 20. That is, in the third function block 8C, an actually measured second CT value contained in the image data is compared with the second reference CT value so as to detect the position of the rod. Thereafter, a region of interest (ROI) is defined in a fourth function block 10A. Thus, the ROI data obtained in the fourth function block 10A is directly supplied to a display controller 5A as position data, and also this ROI data is averaged in an averaging means 5B. The resultant averaged ROI data is furnished as the CT value data to the display controller 5A. As a result, both the position data on ROI and CT value data are supplied to the display unit 6, and the CT image is represented as in FIG. 6.

The above-described functions 8A to 8C are executed in the CT value measuring unit 8 shown in FIG. 6. The function 10A is performed in the ROI designating unit 10. Similarly, the respective functions 5A and 5B are carried out in the image forming unit 5.

SECOND AUTOMATIC ROI SETTING OPERATION

Figure 16:
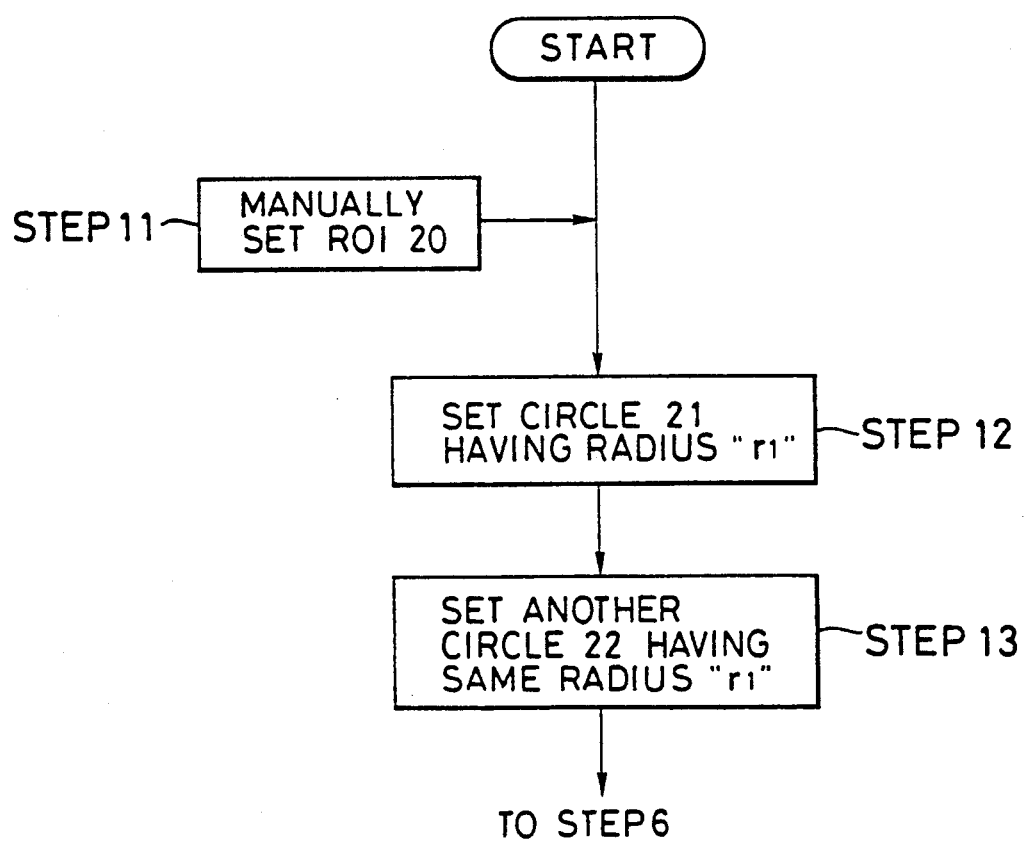
FIG. 16 is a flowchart for explaining an automatic ROI setting method according to a second preferred embodiment of the invention.

In FIG. 16, there is shown a flowchart for explaining an automatic ROI setting operation according to a second preferred embodiment of the invention.

Figure 17:
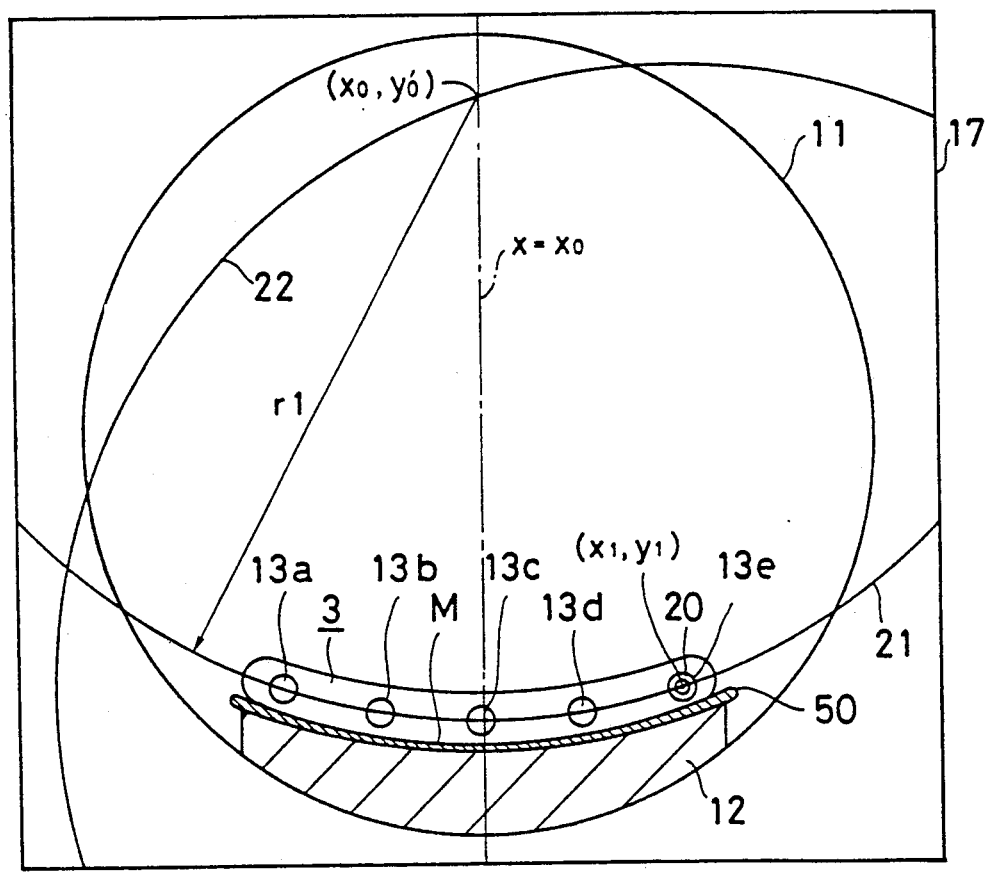
FIG. 17 is an illustration for explaining how to manually and automatically set ROIs according to the second automatic ROI setting method shown in FIG. 16.

As apparent from FIG. 17, a sheet-shaped material 50 having a substantially same curvature as that of the major surface "M" of the phantom 3 is interposed between the phantom 3 and couch plate 12, under which conditions ROI can be automatically set in accordance with the second ROI setting method. First, as shown in the CT image of FIG. 17, a region of interest "20" is manually set by an operator with respect to one rod "13e" on the CT image (step 11). Thereafter, as illustrated in FIG. 17, a circle 21 having a radius equal to the above-described radius "r1" employed in the first ROI setting method (see FIG. 9) is set with respect to a center point $(x_i, y_i)$ of ROI 20 set in the previous step 11 (step 12). Another circle 22 having a radius "r1" is set with respect to a cross point $(x_o', y_o')$ between the set circle 21 and a straight line $x = x_o$ as a center (step 13).

Subsequently, the last-mentioned circle 22 is similarly handled as the previous circle 16 shown in FIG. 9 according to the first preferred embodiment, and the further process is continued to the step 6 as defined in FIG. 7.

In accordance with the second preferred embodiment, there are the following particular advantages in case that, for instance, the sheet-shaped material 50 which will disturb the execution of the automatic ROI setting operation according to the present invention is interposed between the couch plate 12 and phantom 3, namely the CT value of the base portion 15 of the phantom 3 cannot be discriminated from the CT values to other constituting elements according to the automatic ROI setting method defined in the flowchart of the first preferred embodiment. That is to say, once ROI 20 is set in a manual operation by an operator, the subsequent ROI (corresponding to ROI 18 shown in FIG. 12) can be automatically set. As a consequence, the second preferred embodiment is suitable for the actual diagnostic operation by employing the computerized tomographic image diagnostic apparatus.

Third Automatic ROI Setting Operation

An automatic ROI setting operation according to a third preferred embodiment of the invention will now be described with reference to FIGS. 18 and 19.

Figure 18:
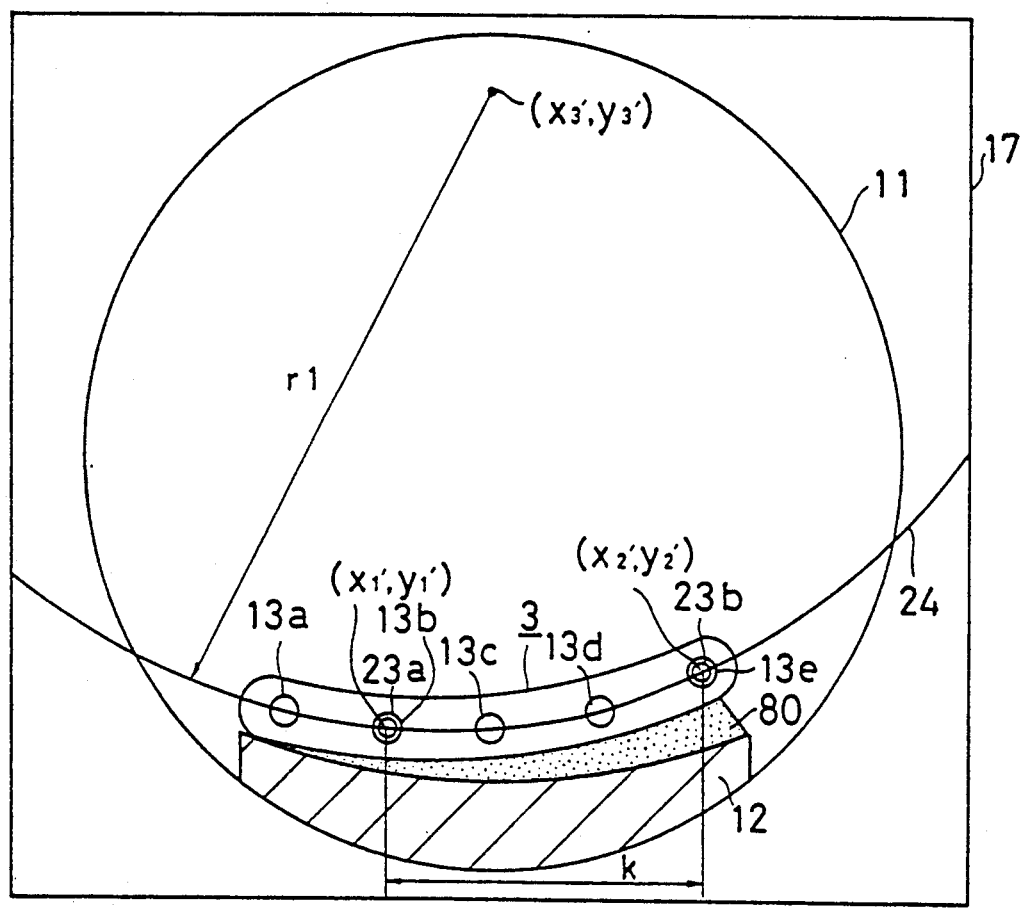
FIG. 18 is an illustration for representing how to manually and automatically set ROIs according to a third automatic ROI setting method; and, FIG. 19 is a flowchart for explaining the third automatic ROI setting method of the present invention.
Figure 19:
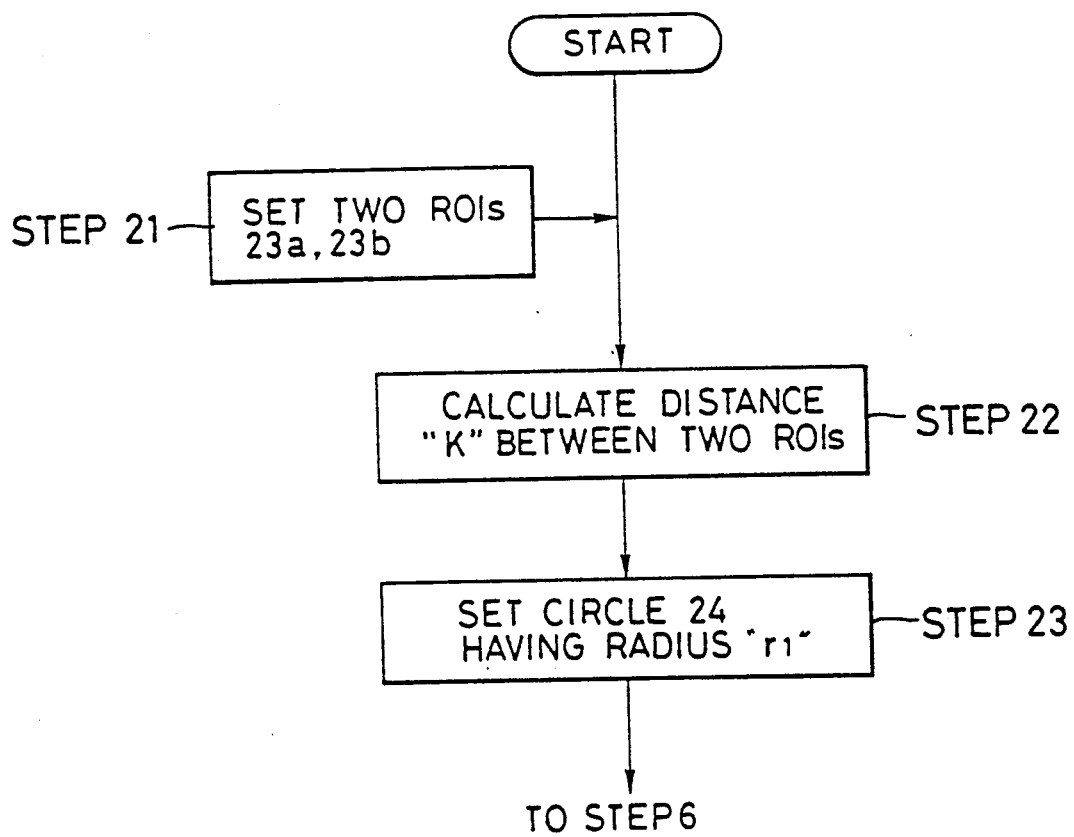

As apparent from FIG. 18, since an impeding article 80 for the first ROI setting operation is interposed between the phantom 3 and couch 12, the first automatic ROI setting operation cannot be directly applied to FIG. 18. FIG. 19 is a flowchart for explaining the third preferred embodiment. In a first step 21, a plurality of ROIs, for instance, two ROIs 23a and 23b are set in a manual way by an operator with respect to two rods 13b and 13e on the CT image shown in FIG. 18. Thereafter, coordinates of center points of two ROIs 23a and 23b are set to be $(x_1', y_1')$ and $(x_2', y_2')$ respectively, and a distance "k" between two ROIs 23a and 23b is calculated based on the following equation (9) in step 22:

$$k = \sqrt{(x_1' - x_2')^2 + (y_1' - y_2')^2} \tag{9}$$

Thereafter, a circle 24 having a radius of "r1" is newly set with respect to a point $(x_3', y_3')$ as a center point, which is calculated by the following equations (10) and (11) by utilizing two coordinates $(x_1', y_1')$ and $(x_2', y_2')$ of center points of two ROIs 23a and 23b, and also the distance "k" between two points calculated by the previous equation (9) in a next step 23.

$$x_3' = \frac{x_1 + x_2}{2} + \frac{\sqrt{r_1^2 + k^2/4} \; (y_2 - y_1)}{k} \tag{10}$$

$$y_3' = \frac{y_1 + y_2}{2} + \frac{\sqrt{r_1^2 + k^2/4} \; (y_2 - y_1)}{k} \tag{11}$$

Subsequently, the resultant circle 24 is similarly used as the previous circle 16 shown in FIG. 9 according to the first preferred embodiment, and then the further process is continued to the step 6 of the first preferred embodiment (see FIG. 7).

While has been described in detail, the third ROI setting method can be executed even in such a practical difficulty of the CT imaging diagnosis, namely the impeding article 80 interposed between the phantom 3 and couch plate 12. Accordingly, the third automatic ROI setting operation can provide a more particular merit than in the second automatic ROI setting operation in view of the practical diagnosis.

As previously described in detail, in accordance with the automatic ROI setting system of the invention, both an object under medical examination and the phantom containing a plurality of reference substances are simultaneously imaged by way of an X-ray CT apparatus, or an MRI imaging apparatus so as to measure the gradations of the respective pixels within a portion of the image region. Then, the region having the gradation corresponding to the gradation range of the phantom is recognized as a portion of the phantom. Based on the position of this phantom portion as a reference, a predetermined pattern, for instance, a circle having a preselected radius is set, around which all of these reference substances are located. Since the respective positions of the reference substances within the phantom are predetermined, all of the reference substances are always present on the pattern if the position of the phantom is actually recognized on the CT image and also the above-described preselected pattern is set with respect to the actual positions of the reference substances as the reference. After the pattern has been set, the gradations of all of the pixels on the pattern are measured. Then, the position of the region having such a gradation corresponding to the gradation range of the reference substance is recognized as the position of the reference substance. As a consequence, the region of interest is set with respect to the positions of the reference substances as the reference values, so that the region of interest can be automatically set according to the invention.

As apparent from the foregoing descriptions, the present invention is not limited to the previous preferred embodiments, but may be modified, changed, and substituted without departing from the technical spirit and scope of the invention. For instance, the plate-like curved phantom was interposed between the object under examination and the couch plate in the preferred embodiments. The shape of the phantom is not restricted thereto, but may be, for example, a disk. Also, although the pattern formed by the image forming unit 5 was the circle, either a straight line or a rectangular shape may be formed, depending upon the shape of the phantom.

While has been described, in accordance with present invention, the normal phantom containing a plurality of reference substances is employed and the positions of the reference substances are recognized, and thus the region of interest can be automatically set without any cumbersome manual operation.

What is claimed is:

1. A method for automatically setting a region of interest in a tomographic image comprising the steps of:
    imaging both an object under medical examination and a phantom made of a plurality of reference substances and a base portion so as to produce a tomographic image, said base portion having a first known CT (computerized tomographic) value and said reference substances each having a second known CT value different from said first CT value;
    automatically detecting an intensity distribution of CT values which comprises intensity data corresponding to said reference substances;
    automatically eliminating from said intensity distribution a threshold level component to obtain intensity data for only said reference substances; and
    automatically determining regions of interest in response to said intensity data for only said reference substances.

2. A method as claimed in claim 1, wherein said imaging step is performed by utilizing an X-ray CT imaging apparatus.

3. A method as claimed in claim 1, wherein said imaging step is performed by utilizing a nuclear magnetic resonance imaging apparatus.

4. A method as claimed in claim 1, wherein said reference substances of the phantom are rods.

5. A method as claimed in claim 1, wherein said base portion of the phantom is an urethane resin.

6. A tomographic image diagnostic apparatus comprising:
    means for imaging both an object under medical examination and a phantom made of a plurality of reference substances and a base portion so as to produce tomographic image data from which a tomographic image may be obtained, said base portion having a first known CT (computerized tomographic) value and said reference substance having a second known CT value different from said first CT value;
    memory means for storing said tomographic image data;
    means for detecting an intensity distribution of CT values which comprises image data corresponding to said reference substances;
    means for eliminating from said intensity distribution a threshold level component to obtain image data for only said reference substances; and
    means for determining regions of interest in response to said image data for only said reference substances.

7. An apparatus as claimed in claim 6, wherein said tomographic image imaging means is an X-ray CT imaging apparatus.

8. An apparatus as claimed in claim 6, wherein said tomographic image imaging means is a nuclear magnetic resonance imaging apparatus.

9. An apparatus as claimed in claim 6, wherein said reference substances of the phantom are rods.

10. An apparatus as claimed in claim 6, wherein said base portion of the phantom is an urethane resin.

11. An apparatus as claimed in claim 6, further comprising:
    means for displaying said tomographic image and said region of interest superimposed thereon in response to said tomographic image data.

12. A tomographic image diagnostic apparatus comprising:
    image memory means for storing tomographic image data on an object under medical examination and also a phantom made of a plurality of reference substances and a base portion thereof;
    storage means for previously storing a first reference CT (computerized tomographic) value used for said base portion of the phantom, and also a second reference CT value used for each of said reference substances;
    first detecting means for detecting a position of said phantom by comparing an actually measured first CT value of said base portion with said first reference CT value previously stored in said storage means;
    processing means for performing both profile and filtering processes on said detected position of the phantom so as to obtain processed positional data of the phantom;
    second detecting means for detecting positions of said reference substances contained in said phantom by comparing an actually measured second CT value of each of said reference substances with said second reference CT value previously stored in said storage means; and,
    defining means for automatically defining a position of a region of interest with respect to said tomographic image data based upon the detected positions of said reference substances.

13. A tomographic image diagnostic apparatus as claimed in claim 12, further comprising:
    averaging means for averaging said defined position of the region of interest so as to obtain a CT value of said region of interest; and, display means for displaying a tomographic image of said object and phantom, and also said region of interest superimposed thereon in response to said defined position and said CT value of said region of interest.

14. A method for automatically setting a region of interest in a tomographic image comprising the steps of:
imaging both an object under medical examination and a phantom made of a plurality of reference substances and a base portion so as to produce a tomographic image, said base portion having a first known CT (computerized tomographic) value and said reference substances each having a second known CT value different from said first CT value;
manually setting a region of interest at the position of one of said reference substances on the tomographic image;
automatically setting a pattern having a predetermined shape on the tomographic image based upon said manually set region of interest;
automatically identifying pixels having the second known CT value located on the pattern so as to recognize positions of the reference substances; and
automatically setting regions of interest in the tomographic image based upon the recognized positions of said reference substances.

15. A method for automatically setting a region of interest in a tomographic image comprising the steps of:
imaging both an object under medical examination and a phantom made of a plurality of reference substances and a base portion so as to produce a tomographic image, said base portion having a first known CT (computerized tomographic) value and said reference substances each having a second known CT value different from said first CT value;
manually setting first and second regions of interest at the positions of first and second ones of said reference substances on the tomographic image;
automatically calculating a distance between center points of said first and second regions of interest;
automatically setting a pattern having a predetermined shape on the tomographic image based upon said centers of positions and said distance;
automatically identifying pixels having the second known CT value located on the pattern so as to recognize positions of the reference substances; and
automatically setting regions of interest in the tomographic image based upon the recognized positions of said reference substances.

* * * * *